US012673149B2

(12) United States Patent
He

(10) Patent No.: US 12,673,149 B2
(45) Date of Patent: Jul. 7, 2026

(54) SUCTION DEVICE FOR SUCKING OBSTRUCTION IN RESPIRATORY TRACT AND USE METHOD THEREFOR

(71) Applicant: DCSTAR INC, New York, NY (US)

(72) Inventor: Ligui He, New York, NY (US)

(73) Assignee: DCSTAR INC, New York, NY (US)

( * ) Notice: Subject to any disclaimer, the term of this patent is extended or adjusted under 35 U.S.C. 154(b) by 320 days.

(21) Appl. No.: 18/305,560

(22) Filed: Apr. 24, 2023

(65) Prior Publication Data

US 2023/0293803 A1     Sep. 21, 2023

Related U.S. Application Data

(63) Continuation of application No. 17/393,187, filed on Aug. 3, 2021, now Pat. No. 11,633,530.

(51) Int. Cl.
| | |
|---|---|
| *A61M 1/00* | (2006.01) |
| *A61M 16/00* | (2006.01) |
| *A61M 16/06* | (2006.01) |
| *A61B 17/50* | (2006.01) |

(52) U.S. Cl.
CPC .......... *A61M 1/67* (2021.05); *A61M 16/0009* (2014.02); *A61M 16/06* (2013.01); *A61B 17/50* (2013.01); *A61M 2210/1025* (2013.01)

(58) Field of Classification Search
CPC .... A61M 39/10; A61M 16/003; A61M 16/06; A61M 1/67; A61M 1/81; A61B 17/50
See application file for complete search history.

(56) References Cited

U.S. PATENT DOCUMENTS

| | | | | |
|---|---|---|---|---|
| 3,809,079 A | * | 5/1974 | Buttaravoli | ....... A61M 16/0488 |
| | | | | 128/207.14 |
| 3,939,830 A | | 2/1976 | da Costa | |
| 3,946,736 A | | 3/1976 | Neward | |
| 4,196,728 A | | 4/1980 | Granite | |
| 4,580,816 A | * | 4/1986 | Campbell | ............. F16L 37/025 |
| | | | | 285/321 |

(Continued)

FOREIGN PATENT DOCUMENTS

| | | | | |
|---|---|---|---|---|
| CN | 108498883 | 9/2018 | | |
| CN | 112169109 | 1/2021 | | |
| CN | 112169109 A | * | 1/2021 | ........ A61M 16/0003 |

OTHER PUBLICATIONS

English Translation of Liu (CN 112169109 A) (Year: 2021).*

*Primary Examiner* — Nilay J Shah
(74) *Attorney, Agent, or Firm* — HSML P.C.

(57) ABSTRACT

A suction device includes a negative pressure generator, a connector and a mask; the negative pressure generator comprises a housing and a piston rod, wherein the housing is internally provided with a cavity, an upper end of the housing is provided with an avoidance hole communicated with the cavity, and a lower end thereof is provided with an opening communicated with the cavity; the piston rod comprises a push-pull rod and a piston sleeved on the push-pull rod, an upper end of the push-pull rod runs through the avoidance hole, and the piston is movably and hermetically connected to an inner side wall of the housing by means of a sealing ring; an upper side of the mask is provided with a through first connecting cylinder, and a lower side thereof is provided with a flexible annular pad configured to fit with the face.

21 Claims, 5 Drawing Sheets

(56)  References Cited

U.S. PATENT DOCUMENTS

| | | | |
|---|---|---|---|
| 4,971,053 A * | 11/1990 | Tarrats .................. | A61B 17/50 |
| | | | 128/206.28 |
| 5,609,149 A | 3/1997 | Takach | |
| 5,628,305 A * | 5/1997 | Melker ............ | A61M 16/0075 |
| | | | 128/205.15 |
| 5,782,837 A | 7/1998 | York | |
| 9,932,936 B2 | 4/2018 | Klonis et al. | |
| 10,052,115 B2 | 8/2018 | Lih | |
| 10,271,998 B2 | 4/2019 | LaVon et al. | |
| 10,675,393 B1 * | 6/2020 | Carver .................. | A61B 17/24 |
| 2006/0243676 A1 * | 11/2006 | Swift ........................ | A61P 7/04 |
| | | | 366/241 |
| 2012/0024293 A1 * | 2/2012 | Maguire ........... | A61M 16/0486 |
| | | | 128/207.14 |
| 2015/0190158 A1 | 7/2015 | Lih | |
| 2018/0318516 A1 * | 11/2018 | Phipps .............. | A61M 5/31511 |
| 2019/0388641 A1 | 12/2019 | Bowsher | |
| 2020/0306420 A1 | 10/2020 | Carver | |

* cited by examiner

SUCTION DEVICE FOR SUCKING OBSTRUCTION IN RESPIRATORY TRACT AND USE METHOD THEREFOR

CROSS REFERENCE

This application is a continuation application of U.S. application Ser. No. 17/393,187, filed Aug. 3, 2021, which is incorporated by reference.

TECHNICAL FIELD

The disclosure relates to the technical field of medical apparatuses, and in particular, to a suction device for sucking an obstruction in a respiratory tract and a use method therefor.

BACKGROUND

Foreign body airway obstruction (FBAO) is a rare but treatable cause of accidental death. Asphyxiation caused by an obstruction in a respiratory tract is a life-threatening emergency. If first aid is not given within 4-6 minutes, it often causes the breathing to stop and is fatal; and even if the life is saved, it will often cause irreversible damage due to lack of oxygen for an excessively long time. Therefore, in the rescue, it is necessary to race against the clock to remove the respiratory tract obstruction due to various causes, to make the airway unblocked, ensure that the wounded can be evacuated in a timely and safe manner, and provide the wounded with opportunities of further treatment. Because asphyxiated patients are initially conscious and responsive, there is often an opportunity to take life-saving interventions as early as possible. At present, the most widely used method is the "Heimlich" abdominal thrust method, but this method requires professional training, and may not everyone can use this method correctly. In addition, the "Heimlich" abdominal thrust method may cause serious collateral consequences, such as rupture, tearing and bleeding of the abdominal or thoracic viscera, and rib fractures.

Therefore, some devices and methods for sucking out foreign bodies that block the respiratory tract, which are suitable for use and implementation by the general public, have been designed in the industry. A U.S. patent with an application No. US 20200306420 A1 discloses a suction device. Although this device can help the general public to quickly rescue an asphyxiated patient with respiratory tract obstruction, it still has the following shortcomings:

1) Such a device is provided with an elastic throat tube, and the elastic throat tube has a high hardness and a long size, so that a user is prone to fear after seeing the elastic throat tube. More importantly, the device is likely to cause secondary injury to a patient during an actual asphyxiation operation. Specifically, in the process of inserting the elastic throat tube into the respiratory tract, it is very easy to cause the elastic throat tube to scratch the oropharynx or push an obstructing foreign body in due to panic. In addition, because of the existence of the elastic throat tube, the mask may not completely fit with the face, and a vacuum-like environment cannot be formed, affecting a use effect.

2) Such a device needs to be manually pulled repeatedly in use to form a sufficiently large negative pressure in the device, which requires a rescuer's arm to maintain mechanical swing at a relatively high frequency. However, in actual use, due to factors such as friction and a rescuer's physical strength, the rescuer's frequency of pulling the device is very likely to be insufficient, so that a sufficient negative pressure cannot be formed in the device, resulting in failure of the rescue.

3) Such a device is further provided with a material collection container configured to collect extracted foreign bodies. The material collection container needs to be connected to a duckbill check valve, and the duckbill check valve not only needs to perform the function of an air outlet, but also needs to enable inhaled mucus and other impurities to flow out. However, because an opening at an air outlet end of the duckbill check valve is relatively small, the opening is very likely to be blocked by foreign bodies, thereby affecting a use effect of the device.

SUMMARY

A technical problem to be solved by the disclosure is to provide a suction device for sucking an obstruction in a respiratory tract, with operations performed in a simpler and labor-saving manner and a large suction force. In the case that the "Heimlich" rescue method cannot be effectively implemented, the suction device can be used to implement rapid and effective auxiliary rescue for an asphyxiated patient with respiratory tract obstruction.

Another technical problem to be solved by the disclosure is to provide a method for using the suction device described above.

To solve the above-mentioned technical problems, the technical solution used by the disclosure is to provide a suction device for sucking an obstruction in a respiratory tract, wherein the suction device comprises a negative pressure generator and a mask, and the mask is communicated with the negative pressure generator by means of a connector; the negative pressure generator comprises a housing and a piston rod movably inserted in the housing, wherein the housing is internally provided with an axially through cavity, an upper end of the housing is provided with an avoidance hole communicated with the cavity, and a lower end thereof is provided with an opening communicated with the cavity; the piston rod comprises a push-pull rod and a piston sleeved on the push-pull rod, an upper end of the push-pull rod runs through the avoidance hole, and an outer side wall of the piston is movably and hermetically connected to an inner side wall of the housing; an upper side of the mask is provided with a through first connecting cylinder, and a lower side thereof is provided with a flexible annular pad configured to fit with the face; and an upper side of the connector is hermetically connected to the opening, and a lower side thereof is hermetically connected to the first connecting cylinder.

Through the suction device of the above-mentioned technical solution, the piston rod can be pushed to the bottommost end first, and then the flexible annular pad of the mask surrounds the mouth of an asphyxiated patient and fits closely with the face; then the mask is held with one hand to keep a seal between the mask and the face, and the piston rod is quickly pulled upward with the other hand to form a strong vacuum suction in the cavity of the housing; then the entire suction device is quickly pulled up with the hand originally holding the mask to release the internal vacuum suction; and after the mask completely leaves from the face, the piston rod is pushed to the bottommost end again, and air and foreign bodies in the housing are discharged. The obstruction in the respiratory tract of the asphyxiated patient can be quickly extracted by repeating the above-mentioned operation steps. Therefore, effective auxiliary rescue is performed for an asphyxiated patient in a simpler and labor-saving way without inserting an elastic throat tube into the respiratory tract of the asphyxiated patient.

In the suction device for sucking an obstruction in a respiratory tract provided in the disclosure, the connector comprises a base plate, an upper side of the base plate is provided with a hollow upper connecting cylinder, the upper connecting cylinder is inserted in the opening, and an outer side of the upper connecting cylinder is hermetically connected to an inner side of the opening.

In the suction device for sucking an obstruction in a respiratory tract provided in the disclosure, the connector comprises a base plate, a lower side of the base plate is provided with a hollow lower connecting cylinder, the first connecting cylinder is inserted in the lower connecting cylinder, and an outer side of the first connecting cylinder is hermetically connected to an inner side of the lower connecting cylinder.

In the suction device for sucking an obstruction in a respiratory tract provided in the disclosure, the base plate is provided with a through air vent.

In the suction device for sucking an obstruction in a respiratory tract provided in the disclosure, the connector comprises a base plate; an upper side of the base plate is provided with a hollow upper connecting cylinder, the upper connecting cylinder is inserted in the opening, and an outer side of the upper connecting cylinder is hermetically connected to an inner side of the opening; a lower side of the base plate is provided with a hollow lower connecting cylinder, the first connecting cylinder is inserted in the lower connecting cylinder, and an outer side of the first connecting cylinder is hermetically connected to an inner side of the lower connecting cylinder; and a central axis of the lower connecting cylinder and a central axis of the upper connecting cylinder form a certain included angle. In this way, in the process of using the suction device, the piston rod may does not need to be pulled up vertically, but is pulled upward obliquely, which is more conducive to exerting a force on a rescuer with a lower height.

In the suction device for sucking an obstruction in a respiratory tract provided in the disclosure, the mask consists only of a hollow mask body, the first connecting cylinder and the flexible annular pad; and the mask body is connected to a lower end of the first connecting cylinder, and the flexible annular pad is arranged on a lower edge of the mask body.

In the suction device for sucking an obstruction in a respiratory tract provided in the disclosure, the mask body is hemispherical, a lower edge of the mask body is circular, and the flexible annular pad is circular. The hemispherical mask body is suitable for the face of an animal, and thus the suction device can be used to rescue an animal (a cat or a dog) asphyxiated due to a respiratory tract obstruction.

In the suction device for sucking an obstruction in a respiratory tract provided in the disclosure, the suction device further comprises an air pressure sensor and a display electrically connected to the air pressure sensor, wherein the display is mounted on an outer side of the housing, and the air pressure sensor is arranged in the connector. The air pressure sensor can measure the negative pressure in the suction device, and the display displays a measurement result. In this way, a rescuer can control a pulling force on the basis of a numerical value displayed on the display for asphyxiated patients with different conditions.

To solve another technical problem mentioned above, the technical solution used by the disclosure is to provide a use method, the use method comprising the following steps:

step S1: pushing a piston rod to a bottommost end;

step S2: a flexible annular pad of a mask surrounding the mouth of an asphyxiated patient and fitting closely with the face;

step S3: then holding the mask with one hand to keep a seal between the mask and the face, and quickly pulling the piston rod upward with the other hand, so as to form a vacuum suction in a cavity of the housing;

step S4: quickly pulling up the entire suction device with the hand originally holding the mask to release the internal vacuum suction;

step S5: after the mask completely leaves from the face, pushing the piston rod to the bottommost end again, and discharging air and foreign bodies in the housing; and repeating steps S2 to S5 until the obstruction in the respiratory tract of the asphyxiated patient is extracted.

In the use method provided in the disclosure, in step S2, the flexible annular pad of the mask surrounds the mouth and nose of the asphyxiated patient and fits closely with the face.

In the use method provided in the disclosure, in step S1, when the piston rod is pushed to the bottommost end, the piston abuts against the connector.

In the use method provided in the disclosure, the top of the push-pull rod is further provided with a handle 1 that can be held by a rescuer; and in step S1, when the piston rod is pushed to the bottommost end, a lower side of the handle 1 abuts against an end side of the avoidance hole.

The disclosure further provides a suction device for sucking an obstruction in a respiratory tract, wherein the suction device comprises a negative pressure generator and a mask, and the mask is communicated with the negative pressure generator by means of a connector; the negative pressure generator comprises a housing and a piston rod movably inserted in the housing, wherein the housing is internally provided with an axially through cavity, an upper end of the housing is provided with an avoidance hole communicated with the cavity, and a lower end thereof is provided with an opening communicated with the cavity; the piston rod comprises a push-pull rod and a piston sleeved on the push-pull rod, an upper end of the push-pull rod runs through the avoidance hole, an outer side wall of the piston is sleeved with a first sealing ring, an inner side wall of the first sealing ring is hermetically connected to an outer side wall of the piston, and an outer side wall of the first sealing ring is movably and hermetically connected to an inner side wall of the housing; an upper side of the mask is provided with a through first connecting cylinder, and a lower side thereof is provided with a flexible annular pad configured to fit with the face; and an upper side of the connector is hermetically connected to the opening, and a lower side thereof is hermetically connected to the first connecting cylinder.

In the suction device for sucking an obstruction in a respiratory tract provided in the disclosure, the outer side wall of the piston is sleeved with a second sealing ring, and a center of the second sealing ring and a center of the first sealing ring both fall on a central axis of the piston; and an inner side wall of the second sealing ring is hermetically connected to the outer side wall of the piston, and an outer side wall of the second sealing ring is movably and hermetically connected to the inner side wall of the housing.

In the suction device for sucking an obstruction in a respiratory tract provided in the disclosure, the connector comprises a base plate, an upper side of the base plate is provided with a hollow upper connecting cylinder, the upper connecting cylinder is inserted in the opening, and an outer side of the upper connecting cylinder is hermetically connected to an inner side of the opening; and a lower side of the base plate is provided with a hollow lower connecting cylinder, the first connecting cylinder is inserted in the lower connecting cylinder, and an outer side of the first connecting cylinder is hermetically connected to an inner side of the lower connecting cylinder.

In the suction device for sucking an obstruction in a respiratory tract provided in the disclosure, the connector is further provided with an opening hole, the opening hole runs through the base plate, a lower end of the opening hole is communicated with the outside, an external check valve is arranged in the opening hole, and the external check valve can allow a gas in the housing of the connector to flow out to the outside.

In the suction device for sucking an obstruction in a respiratory tract provided in the disclosure, the top of the push-pull rod is further provided with a handle that can be held by a rescuer.

In the suction device for sucking an obstruction in a respiratory tract provided in the disclosure, the upper end of the housing is further provided with an exhaust port communicated with the cavity.

In the suction device for sucking an obstruction in a respiratory tract provided in the disclosure, when the piston moves toward the lower end of the housing, air in the housing enters the connector through the upper connecting cylinder, and then flows out from the mask through the air vent and the lower connecting cylinder; and when the piston moves toward the upper end of the housing, the air in the housing flows to the outside from the avoidance hole and the exhaust port.

In the suction device for sucking an obstruction in a respiratory tract provided in the disclosure, the mask is detachably connected to the connector, so that the mask can be replaced with a mask with a different shape and size on the basis of a rescued purpose.

In conclusion, the implementation of the disclosure may achieve at least the following beneficial effects:

1. Compared with the prior art, the suction device of the disclosure removes/omits the elastic throat tube, thereby avoiding the fear of a claustrophobic space to an asphyxiated patient, and fundamentally avoiding the discomfort caused by the insertion of the elastic throat tube into the respiratory tract and the user's fear as well as safety hazards arising from the insertion of the elastic throat tube into the respiratory tract. Moreover, because the elastic throat tube is removed/omitted, the suction device of the disclosure is more safely applied to the rescue of children. In addition, the constraint of the elastic throat tube on the placement of the mask is completely removed, ensuring that the mask perfectly fits with the face.

2. In the process of operating the suction device according to the use method of the disclosure, after the flexible annular pad of the mask surrounds the mouth of the asphyxiated patient and closely fits with the face, the mask is held with one hand to keep a seal between the mask and the face, and the piston rod is quickly pulled upward with the other hand, so that a strong vacuum suction can be formed in a cavity of the housing; and then the mask is quickly lifted up with the hand originally holding the mask to release a negative pressure, so that a strong suction force on the respiratory tract is formed, and the piston rod is pushed to the bottom, so that internal air and foreign bodies can be discharged while the air in the housing is discharged. With the use method of the disclosure, a strong negative pressure can be formed in the housing without repeatedly pulling the piston rod. Because there is no restriction from the elastic throat tube, a rescuer can maximize the strength of his/her arm each time he/she pulls the piston rod, thus ensuring that a sufficient negative pressure is generated in the suction device to form a sufficient vacuum suction, thereby successfully sucking out an obstruction.

3. In the process of operating the suction device according to the use method of the disclosure, when the piston rod is pushed to the bottom, internal air and foreign bodies can be discharged while the air in the housing is discharged, thereby preventing a risk of foreign body backflow. Moreover, compared with the opening at the air outlet end of the duckbill valve, the air vent in the connector has a larger size, thereby being less likely to be blocked. In addition, a material collection container is omitted, which facilitates an increase in the volume of the housing, thereby increasing the air volume in the cavity of the housing, increasing the negative pressure that can be formed during single pulling, generating a greater vacuum suction and achieving a better first aid effect.

BRIEF DESCRIPTION OF THE DRAWINGS

In order to more clearly explain the embodiments of the disclosure or the technical solutions in the prior art, the drawings to be used in the description of the embodiments or the prior art will be briefly introduced below. Obviously, the drawings in the following description are only embodiments of the disclosure. For those of ordinary skill in the art, other drawings may be obtained according to the provided drawings without any creative work.

Figure 1:
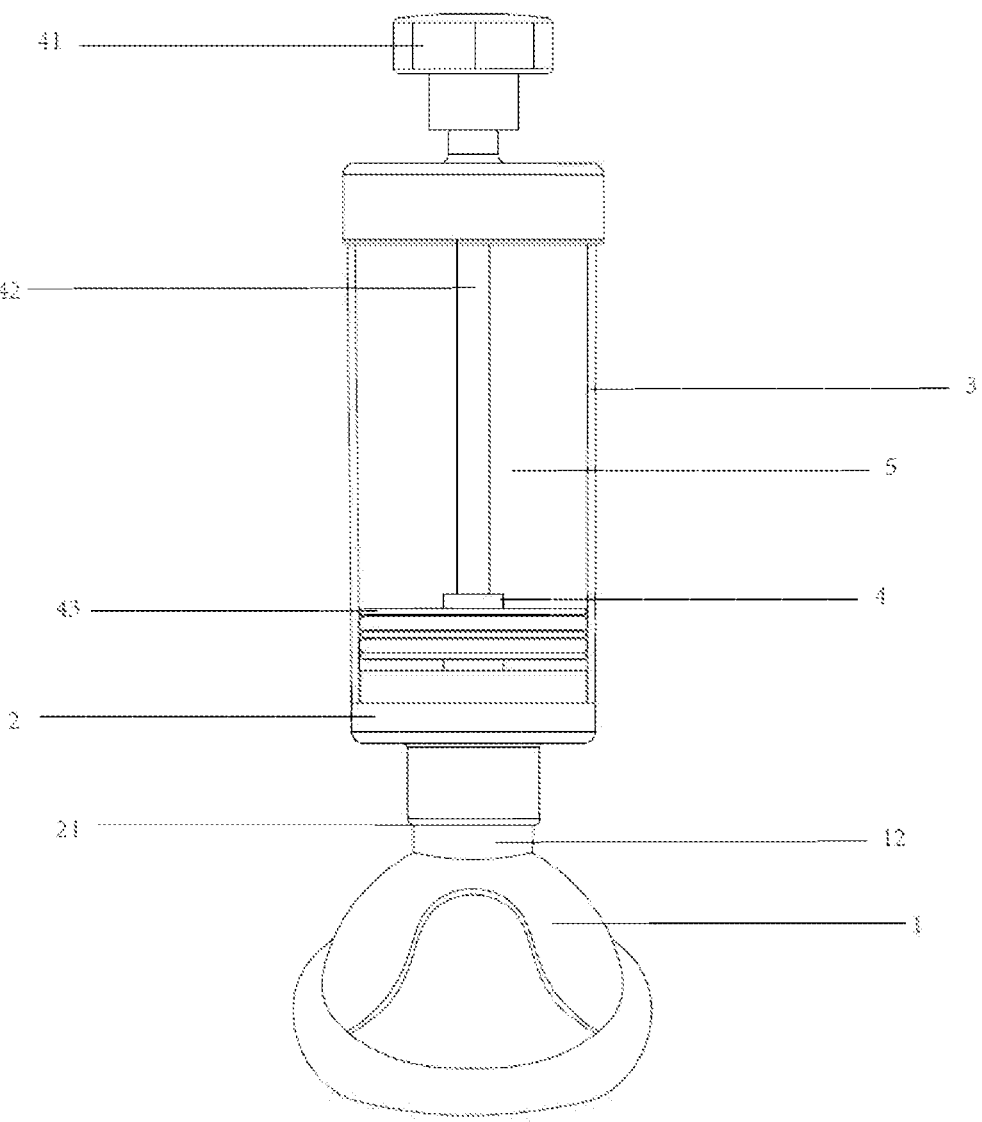
FIG. 1 is a three-dimensional combined schematic diagram of a suction device provided in Embodiment I.

Description of reference numerals in specific implementations:

| Mask | 1 | Flexible annular pad | 11 |
|---|---|---|---|
| First connecting cylinder | 12 | Mask body | 13 |
| Connector | 2 | Lower connecting cylinder | 21 |
| Upper connecting cylinder | 22 | Air vent | 23 |
| base plate | 24 | Display | 25 |
| Air pressure sensor | 26 | Internal check valve | 27 |
| External check valve | 28 | Housing | 3 |
| Opening | 31 | Avoidance hole | 32 |
| Exhaust port | 33 | Piston rod | 4 |

-continued

| Handle | 41 | Push-pull rod | 42 |
| Piston | 43 | First sealing ring | 44 |
| Second sealing ring | 45 | Negative pressure generator | 5 |

DETAILED DESCRIPTION

In order to facilitate understanding of the disclosure, the disclosure will be described more comprehensively below with reference to related drawings. Typical embodiments of the disclosure are given in the drawings. However, the disclosure may be implemented in many different forms, which are not limited to the embodiments described herein. On the contrary, the purpose of providing these embodiments is to make the summary of the disclosure more thorough and comprehensive.

Unless otherwise defined, all technical and scientific terms used herein have the same meaning as commonly understood by those skilled in the technical field of the disclosure. The terms used in the specification of the disclosure herein is for the purpose of describing specific embodiments, and are not intended to limit the disclosure.

Embodiment I

Figure 2:
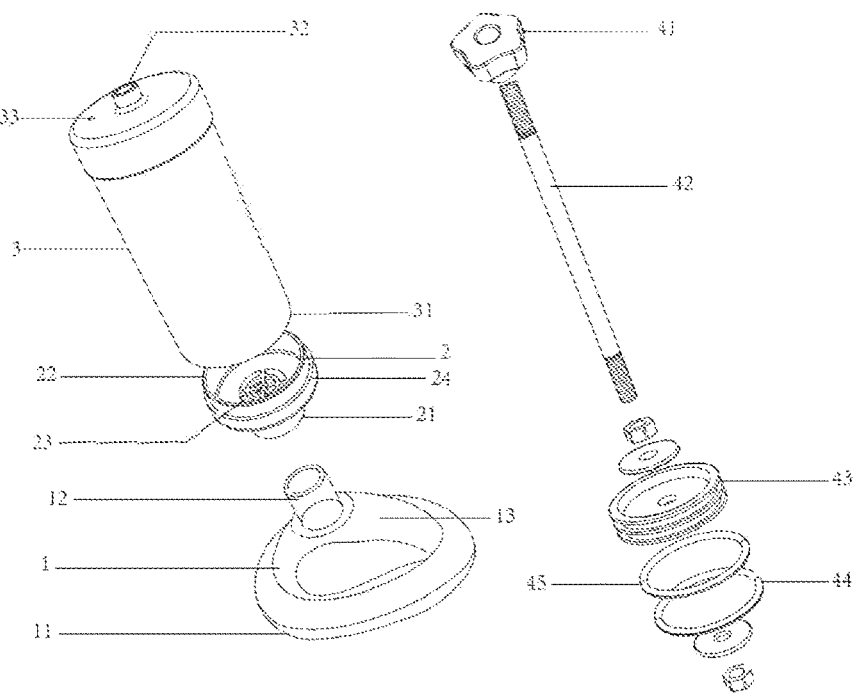
FIG. 2 is a three-dimensional exploded schematic diagram of the suction device provided in Embodiment I.

This embodiment provides a suction device for sucking an obstruction in a respiratory tract. Referring to FIG. 1, FIG. 1 is a three-dimensional combined schematic diagram of a suction device provided in this embodiment. To illustrate an internal structure of the suction device more clearly, a housing 3 is treated in perspective in FIG. 1. As shown in FIG. 1, the suction device comprises a negative pressure generator 5 and a mask 1, wherein the mask 1 is communicated with the negative pressure generator 5 by means of a connector 2. The negative pressure generator 5 comprises a housing 3 and a piston rod 4 movably inserted in the housing 3, wherein the housing 3 is internally provided with an axially through cavity, an upper end of the housing 3 is provided with an avoidance hole 32 communicated with the cavity, and a lower end thereof is provided with an opening 31 communicated with the cavity; and the piston rod 4 comprises a push-pull rod 42 and a piston 43 sleeved on the push-pull rod 42, an upper end of the push-pull rod 42 runs through the avoidance hole 32, and an outer side wall of the piston 43 is movably and hermetically connected to an inner side wall of the housing 3 by means of a sealing ring. Referring to FIG. 2, FIG. 2 is a three-dimensional exploded schematic diagram of the suction device provided in this embodiment. As shown in FIG. 2, an upper side of the mask 1 is provided with a through first connecting cylinder 12, and a lower side thereof is provided with a flexible annular pad 11 configured to fit with the face. In this embodiment, the mask 1 consists only of a hollow mask body 13, the first connecting cylinder 12 and the flexible annular pad 11; and the mask body 13 is connected to a lower end of the first connecting cylinder 12, and the flexible annular pad 11 is arranged on a lower edge of the mask body 13. In this embodiment, an upper side of the connector 2 is hermetically connected to the opening 31. Specifically, referring to FIG. 2, the connector 2 comprises a base plate 24, an upper side of the base plate 24 is provided with a hollow upper connecting cylinder 22, the upper connecting cylinder 22 is inserted in the opening 31, and an outer side of the upper connecting cylinder 22 is hermetically connected to an inner side of the opening 31 (referring to FIG. 1). In this embodiment, a lower side of the connector 2 is hermetically connected to the first connecting cylinder 12. Specifically, referring to FIG. 2, a lower side of the base plate 24 is provided with a hollow lower connecting cylinder 21, the first connecting cylinder 12 is inserted in the lower connecting cylinder 21, and an outer side of the first connecting cylinder 12 is hermetically connected to an inner side of the lower connecting cylinder 21 (referring to FIG. 1). Still referring to FIG. 2, the base plate 24 is provided with a plurality of through air vents 23 so that the upper connecting cylinder 22 is communicated with the lower connecting cylinder 21.

Figure 3:
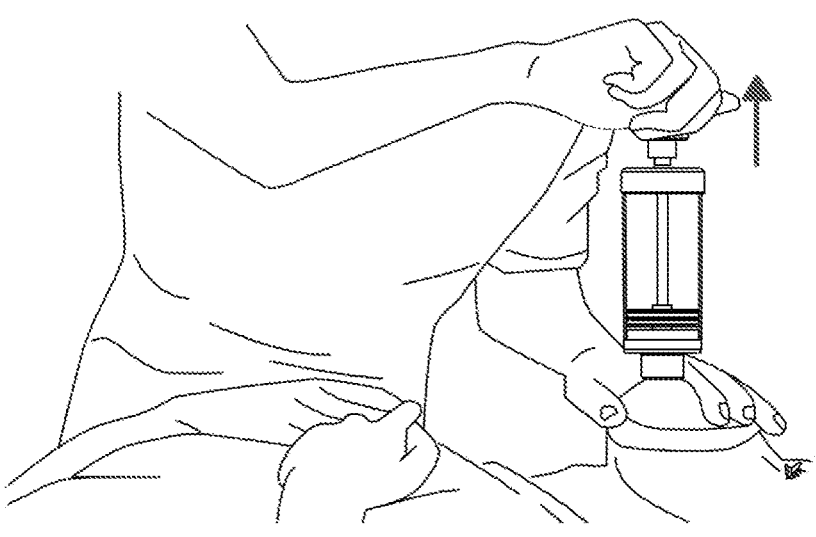
FIG. 3 is a reference diagram (I) of a use state of the suction device provided in Embodiment I.
Figure 4:
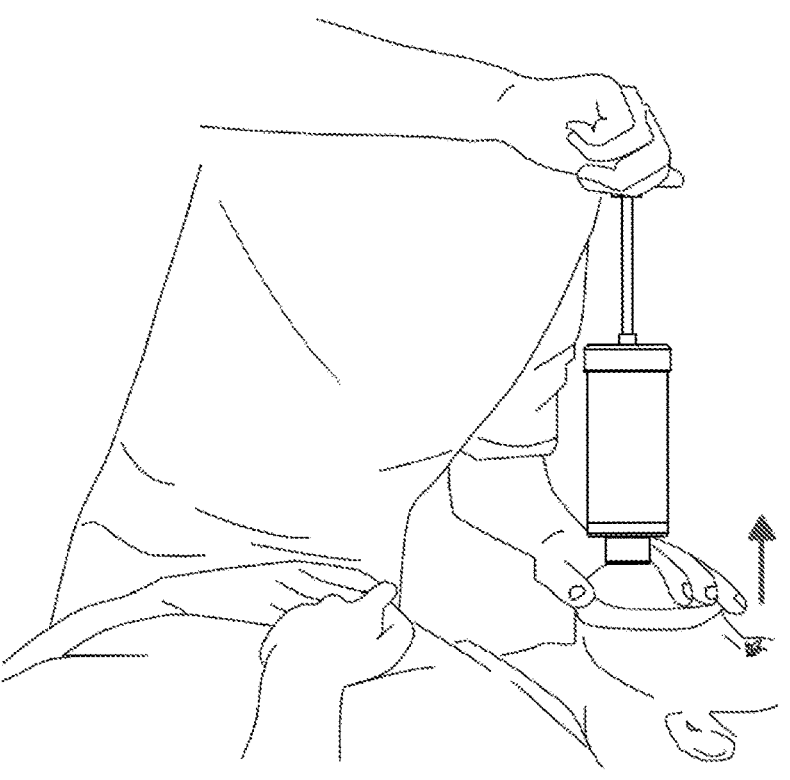
FIG. 4 is a reference diagram (II) of a use state of the suction device provided in Embodiment I.
Figure 5:
FIG. 5 is a reference diagram (III) of a use state of the suction device provided in Embodiment I.

A use method for using the suction device provided in this embodiment to perform auxiliary rescue for an asphyxiated patient comprises the following steps:

step S1: pushing a piston rod 4 to a bottommost end;

step S2: a flexible annular pad 11 of a mask 1 surrounding the mouth of an asphyxiated patient and fitting closely with the face (referring to FIG. 3);

step S3: then holding the mask 1 with one hand to keep a seal between the mask 1 and the face, and quickly pulling the piston rod 4 upward with the other hand, so as to form a vacuum suction in a cavity of the housing 3 (referring to FIG. 4);

step S4: quickly pulling up the entire suction device with the hand originally holding the mask 1 to release the internal vacuum suction (referring to FIG. 5);

step S5: after the mask 1 completely leaves from the face, pushing the piston rod 4 to the bottommost end again, and discharging air and foreign bodies in the housing 3; and repeating steps S2 to S5 until the obstruction in the respiratory tract of the asphyxiated patient is extracted.

In conclusion, compared with the prior art, the implementation of the suction device and the use method therefor provided in this embodiment may achieve at least the following beneficial effects:

1. Effective auxiliary rescue can be performed for an asphyxiated patient in a simpler and labor-saving way without inserting an elastic throat tube into the respiratory tract of the asphyxiated patient.

2. The suction device of this embodiment removes/omits the elastic throat tube, thereby avoiding the fear of a claustrophobic space to the asphyxiated patient, and fundamentally avoiding the discomfort caused by the insertion of the elastic throat tube into the respiratory tract and the user's fear as well as safety hazards arising from the insertion of the elastic throat tube into the respiratory tract. Moreover, because the elastic throat tube is removed/omitted, the suction device of the disclosure is more safely applied to the rescue of children. In addition, the constraint of the elastic throat tube on the placement of the mask 1 is completely removed, ensuring that the mask 1 perfectly fits with the face.

3. In the process of operating the suction device according to the use method of this embodiment, after the flexible annular pad 11 of the mask 1 surrounds the mouth of the asphyxiated patient and closely fits with the face, the mask 1 is held with one hand to keep a seal between the mask 1 and the face, and the piston rod 4 is quickly pulled upward with the other hand, so that a strong vacuum suction can be formed in a cavity of the housing 3; and then the mask 1 is quickly lifted up with the hand originally holding the mask 1 to release a negative pressure, so that a strong suction force on the respiratory tract is formed, and the piston rod 4 is pushed to the bottom, so that internal foreign bodies can be discharged while the air in the housing 3 is discharged. With the use method of the disclosure, a strong negative pressure can be formed in the housing 3 without repeatedly pulling the piston rod 4. Because there is no restriction from the elastic throat tube, a rescuer can maximize the strength of his/her arm each time he/she pulls the piston rod 4, thus ensuring that a sufficient negative pressure is generated in the suction device to form a sufficient vacuum suction, thereby successfully sucking out an obstruction.

4. In the process of operating the suction device according to the use method of this embodiment, when the piston rod 4 is pushed to the bottom, internal foreign bodies can be discharged while the air in the housing 3 is discharged, thereby preventing a risk of foreign body backflow. Moreover, compared with the opening at the air outlet end of the duckbill valve, the air vent 23 in the connector 2 has a larger size, thereby being less likely to be blocked. In addition, a material collection container is omitted, which facilitates an increase in the volume of the housing, thereby increasing the air volume in the cavity of the housing 3, increasing the negative pressure that can be formed during single pulling, generating a greater vacuum suction and achieving a better first aid effect.

Certainly, in some other embodiments, in step S2, the flexible annular pad 11 of the mask 1 may surround the mouth and nose of the asphyxiated patient and fit closely with the face.

In this embodiment, in step S1, when the piston rod 4 is pushed to the bottommost end, the piston 43 abuts against the connector 2.

Certainly, in some other embodiments, in step S1, when the piston rod 4 is pushed to the bottommost end, a lower side of the handle 41 abuts against an end side of the avoidance hole 32.

Further, referring to FIG. 2, the upper end of the housing 3 is further provided with an exhaust port 33 communicated with the cavity. In this way, when the piston rod 4 of a pulling device is pulled and moves upward, the gas in the cavity of the housing 3 can be quickly released from the exhaust port 33, to enable a rescuer to pull the piston rod 4 upward more successfully.

Further, referring to FIG. 2, the negative pressure generator 5 further comprises a first sealing ring 44 and a second sealing ring 45 sleeved outside the piston 43, so that the air tightness between the piston 43 and the housing 3 can be improved. Herein, a center of the second sealing ring 45 and a center of the first sealing ring 44 both fall on a central axis of the piston 43, and the piston 43 is hermetically connected to the housing 3 by means of the first sealing ring 44 and the second sealing ring 45. Specifically, an inner side wall of the first sealing ring 44 is hermetically connected to the outer side wall of the piston 43, and an outer side wall of the first sealing ring 44 is movably and hermetically connected to the inner side wall of the housing 3. An inner side wall of the second sealing ring 45 is hermetically connected to the outer side wall of the piston 43, and an outer side wall of the second sealing ring 45 is movably and hermetically connected to the inner side wall of the housing 3. A gap is actually further reserved between the outer side wall of the piston 43 and the inner side wall of the housing 3.

Further, referring to FIG. 2, the top of the push-pull rod 42 is further provided with a handle 41 that can be held by a rescuer, thereby further improving the operation convenience of the pulling device.

Further, the mask 1 is detachably connected to the connector 2, so that the mask can be replaced with a mask with a different shape and size on the basis of a rescued purpose.

Embodiment II

Figure 6:
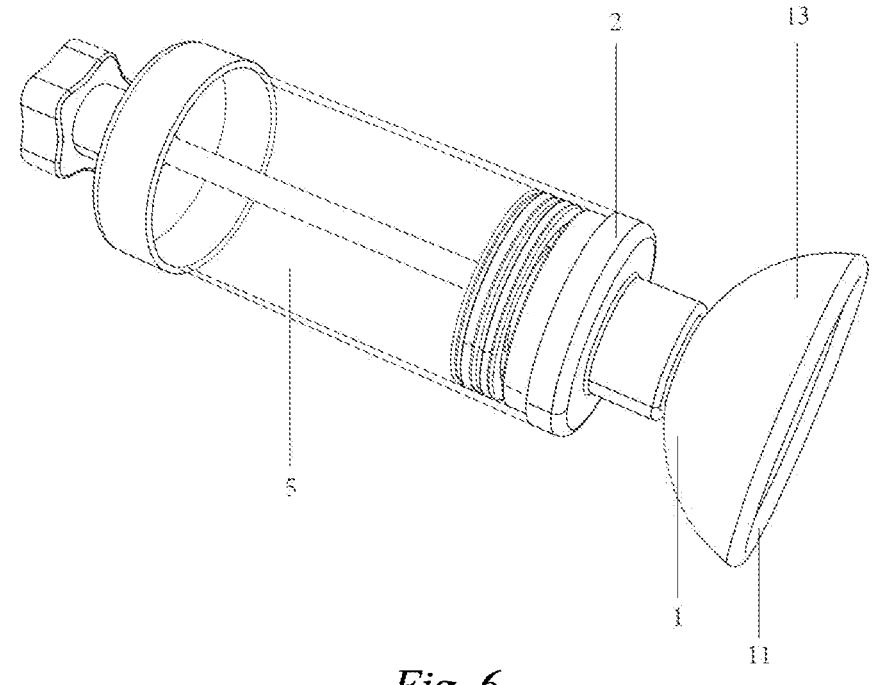
FIG. 6 is a three-dimensional combined schematic diagram of a suction device provided in Embodiment II.

This embodiment provides a suction device for sucking an obstruction in a respiratory tract. The suction device provided in this embodiment differs from the suction device in Embodiment I in that: referring to FIG. 6, FIG. 6 is a three-dimensional combined schematic diagram of a suction device provided in this embodiment; and it can be seen from FIG. 6 that the mask body 13 is hemispherical, a lower edge of the mask body 13 is circular, and the flexible annular pad 11 is circular. The hemispherical mask body 13 is suitable for the face of an animal, and thus the suction device can be used to rescue an animal (a cat or a dog) asphyxiated due to a respiratory tract obstruction.

Embodiment III

Figure 7:
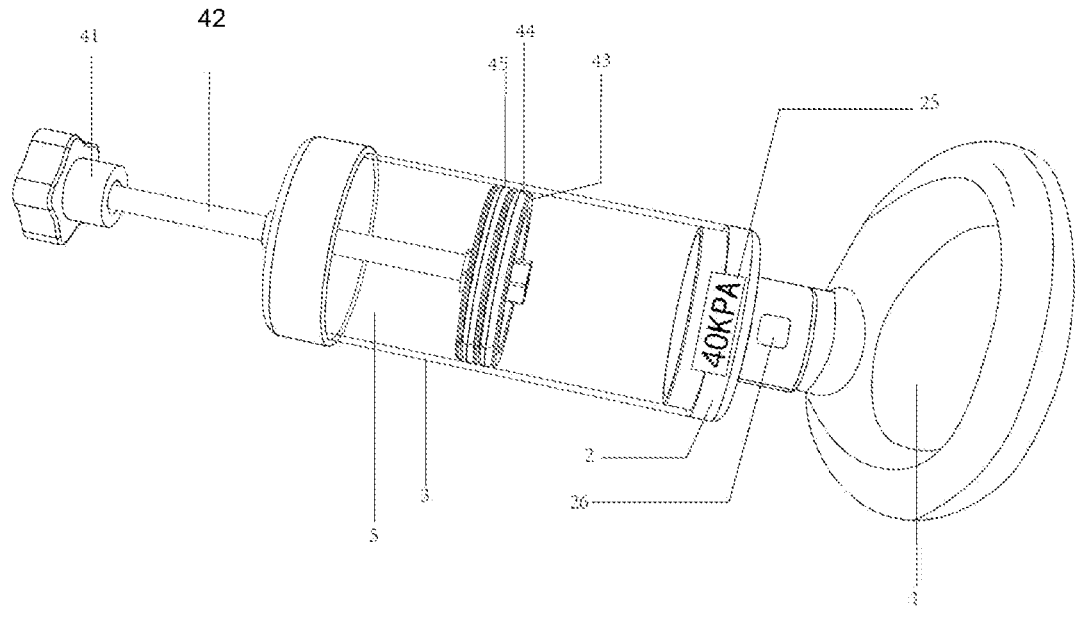
FIG. 7 is a three-dimensional combined schematic diagram of a suction device provided in Embodiment III.

This embodiment provides a suction device for sucking an obstruction in a respiratory tract. The suction device provided in this embodiment differs from the suction device in Embodiment I in that: referring to FIG. 7, FIG. 7 is a three-dimensional combined schematic diagram of a suction device provided in this embodiment; and it can be seen from FIG. 7 that the suction device further comprises an air pressure sensor 26 and a display 25 electrically connected to the air pressure sensor 26, wherein the display 25 is mounted on an outer side of the housing 3, and the air pressure sensor 26 is arranged in the connector 2. The air pressure sensor 26 can measure the negative pressure in the suction device, and the display 25 displays a measurement result. In this way, a rescuer can control a pulling force on the basis of a numerical value displayed on the display 25 for asphyxiated patients with different conditions.

It should be noted that the air pressure sensor 26 is mounted in the lower connecting cylinder 21 of the connector 2, which can not only ensure that the air pressure sensor 26 can detect the magnitude of the negative pressure in the housing 3, but also prevent the air pressure sensor 26 from hindering the movement of the piston rod 4.

Embodiment IV

Figure 8:
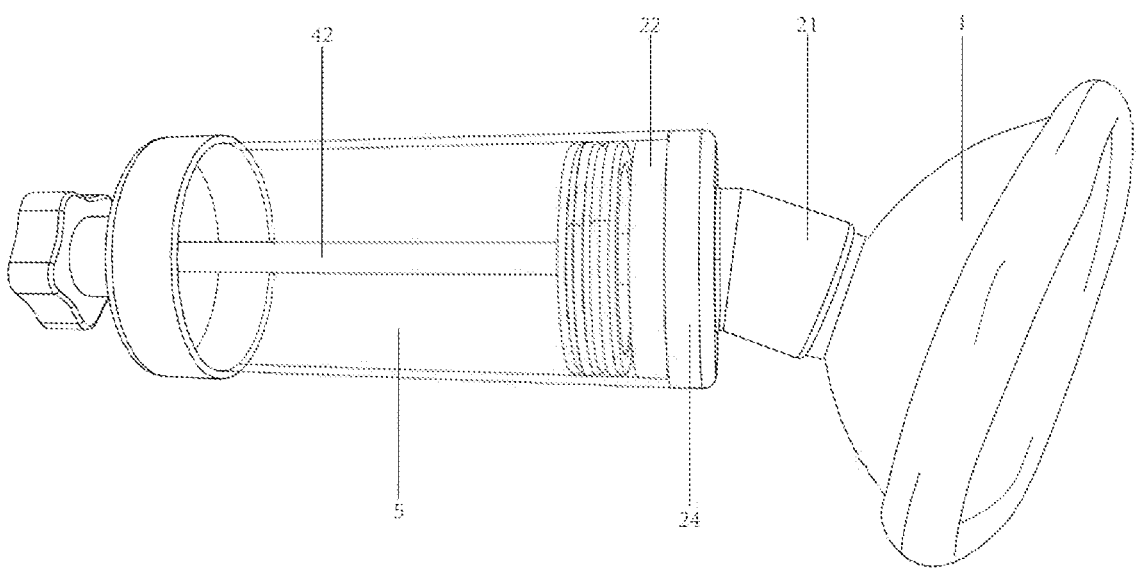
FIG. 8 is a three-dimensional combined schematic diagram of a suction device provided in Embodiment IV.

This embodiment provides a suction device for sucking an obstruction in a respiratory tract. The suction device provided in this embodiment differs from the suction device in Embodiment I in that: referring to FIG. 8, FIG. 8 is a three-dimensional combined schematic diagram of a suction device provided in this embodiment, and it can be seen from FIG. 8 that a central axis of the lower connecting cylinder 21 and a central axis of the upper connecting cylinder 22 form a certain included angle. In this way, in the process of using the suction device, the piston rod 4 may does not need to be pulled up vertically, but the piston rod 4 is pulled upward obliquely, which is more conducive to exerting a force on a rescuer with a lower height.

Embodiment V

Figure 9:
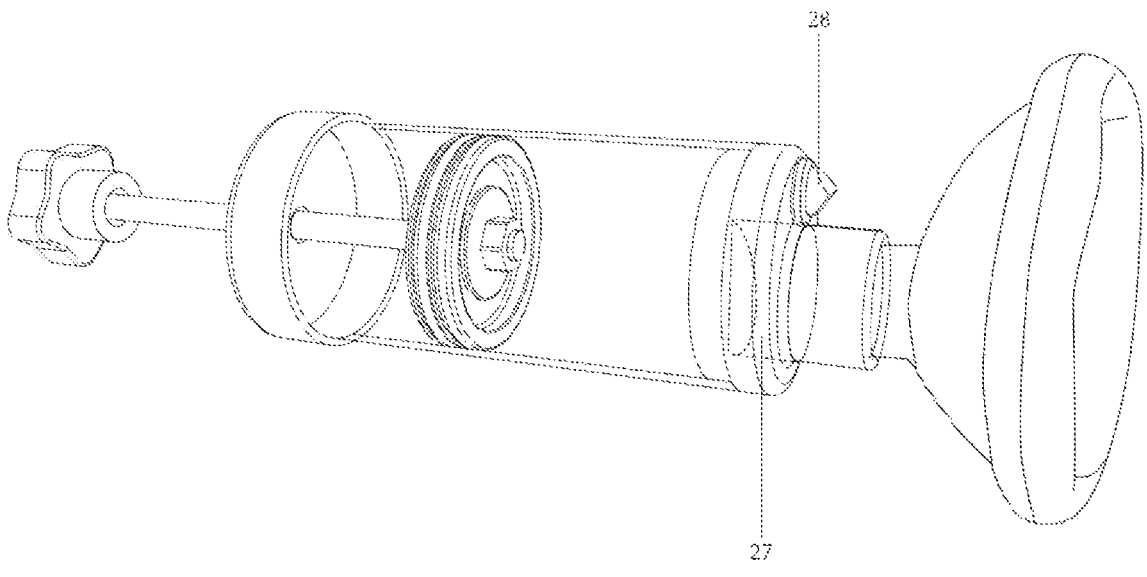
FIG. 9 is a three-dimensional combined schematic diagram of a suction device provided in Embodiment V.

This embodiment provides a suction device for sucking an obstruction in a respiratory tract. The suction device provided in this embodiment differs from the suction device in Embodiment I in that: the connector 2 has a different structure. Specifically, referring to FIG. 9, the connector 2 is further provided with an opening hole, the opening hole runs through the base plate 24, a lower end of the opening hole is communicated with the outside, an external check valve 28 is arranged in the opening hole, and the external check valve 28 can allow a gas in the housing 3 to flow out to the outside. The air vent 23 is a circular through hole, and an internal check valve 27 is arranged in the air vent 23. The internal check valve 27 can allow a gas to flow into the cavity of the housing 3. An upper connecting cylinder 22 and a lower connecting cylinder 21 of the connector 2 are still respectively connected to an opening 31 of the housing 3 and a first connecting cylinder 12 of the mask 1. When the piston rod 4 is pulled upward, the internal check valve 27 in the air vent 23 can allow a gas at a side of the mask 1 to flow into the housing 3. When the piston rod 4 is pushed downward, the external check valve 28 in the opening hole can allow the gas in the cavity of the housing 3 to flow out to the outside, so as to quickly discharge the gas in the housing 3.

The embodiments of the disclosure have been described above with reference to the drawings, but the disclosure is not limited to the above detailed description. The above detailed description is only schematic, not limiting. Under the enlightenment of the disclosure, those of ordinary skill in the art can make many forms without departing from the spirit of the disclosure and the scope of protection of the claims, all of which fall within the protection of the disclosure.

The invention claimed is:

1. A suction device for sucking an obstruction in a respiratory tract, the suction device comprising:
   a negative pressure generator and a mask,
   wherein the mask is communicated with the negative pressure generator by means of a connector;
   the negative pressure generator comprises a housing and a piston rod movably inserted in the housing, the housing is internally provided with an axially through cavity, an upper end of the housing is provided with an avoidance hole communicated with the cavity, and a lower end thereof is provided with an opening communicated with the cavity;
   the piston rod comprises a push-pull rod and a piston sleeved on the push-pull rod, an upper end of the push-pull rod runs through the avoidance hole, and an outer side wall of the piston is movably and hermetically connected to an inner side wall of the housing by means of a sealing ring, such that when the piston moves toward the lower end of the housing, air in the housing enters the connector through an upper connecting cylinder, and then flows out from the mask through an air vent and a lower connecting cylinder; and when the piston moves toward the upper end of the housing, the air in the housing flows to an outside from the avoidance hole and an exhaust port;
   wherein a diameter of the push-pull rod is smaller than a diameter of the housing;
   wherein the mask consists only of a mask body, a through first connecting cylinder, and a flexible annular pad; and the mask body includes an internal space that is connected to a lower end of the through first connecting cylinder, and the flexible annular pad is arranged on a lower edge of the mask body, and
   wherein the mask omits an elastic throat tube such that the elastic throat tube cannot enter a mouth of a patient.

2. The suction device for sucking the obstruction in the respiratory tract according to claim 1, an upper side of the connector is hermetically connected to the opening.

3. The suction device for sucking the obstruction in the respiratory tract according to claim 1, the upper end of the housing is further provided with the exhaust port communicated with the cavity in a way such that when the piston rod is pulled and moves upward, the air in the cavity of the housing is released from the exhaust port to enable a rescuer to pull the piston rod upward.

4. The suction device for sucking the obstruction in the respiratory tract according to claim 1, an upper side of the mask is provided with the through first connecting cylinder, and a lower side thereof is provided with the flexible annular pad configured to fit with a face of a patient.

5. A suction device for sucking an obstruction in a respiratory tract, the suction device comprising:
   a negative pressure generator and a mask, wherein the mask is communicated with the negative pressure generator by means of a connector;
   the negative pressure generator comprises a housing and a piston rod movably inserted in the housing, the housing is internally provided with an axially through cavity, an upper end of the housing is provided with an avoidance hole communicated with the cavity, and a lower end thereof is provided with an opening communicated with the cavity;
   the piston rod comprises a push-pull rod and a piston sleeved on the push-pull rod, an upper end of the push-pull rod runs through the avoidance hole, and an outer side wall of the piston is movably and hermetically connected to an inner side wall of the housing by means of a sealing ring, wherein a top of the push-pull rod is further provided with a handle that can be held by a rescuer; the upper end of the housing is further provided with an exhaust port communicated with the cavity in a way such that when the piston rod is pulled and moves upward, gas in the cavity of the housing is released from the exhaust port to enable a rescuer to pull the piston rod upward;
   wherein the mask consists only of a mask body, a through first connecting cylinder, and a flexible annular pad; and the mask body includes an internal space that is connected to a lower end of the through first connecting cylinder, and the flexible annular pad is arranged on a lower edge of the mask body, and
   wherein the mask omits an elastic throat tube such that the elastic throat tube cannot enter a mouth of a patient.

6. The suction device for sucking the obstruction in the respiratory tract according to claim 5, wherein the flexible annular pad of the mask is configured to surround the mouth and a nose of the patient and to fit closely with a face.

7. The suction device for sucking the obstruction in the respiratory tract according to claim 5, wherein when the piston rod is pushed to a bottommost end, a lower side of the handle abuts against an end side of the avoidance hole.

8. The suction device for sucking the obstruction in the respiratory tract according to claim 5, wherein a lower side of the connector is hermetically connected to the through first connecting cylinder.

9. A suction device for sucking an obstruction in a respiratory tract, the suction device comprising:
   a negative pressure generator and a mask,
   wherein the mask is communicated with the negative pressure generator by means of a connector;
   the negative pressure generator comprises a housing and a piston rod movably inserted in the housing, the housing is internally provided with an axially through cavity, an upper end of the housing is provided with an avoidance hole communicated with the cavity, and a lower end thereof is provided with an opening communicated with the cavity;

the piston rod comprises a push-pull rod and a piston sleeved on the push-pull rod, an upper end of the push-pull rod runs through the avoidance hole, an outer side wall of the piston is sleeved with a first sealing ring, an inner side wall of the first sealing ring is hermetically connected to the outer side wall of the piston, and an outer side wall of the first sealing ring is movably and hermetically connected to an inner side wall of the housing; the outer side wall of the piston is sleeved with a second sealing ring, and a center of the second sealing ring and a center of the first sealing ring both fall on a central axis of the piston;

wherein a diameter of the push-pull rod is smaller than a diameter of the housing; and a mask body includes an internal space that is connected to a lower end of a first connecting cylinder, and a flexible annular pad is arranged on a lower edge of the mask body, and wherein the mask omits an elastic throat tube such that the elastic throat tube cannot enter a mouth of a patient.

10. The suction device for sucking the obstruction in the respiratory tract according to claim 9, wherein an inner side wall of the second sealing ring is hermetically connected to the outer side wall of the piston, and an outer side wall of the second sealing ring is movably and hermetically connected to the inner side wall of the housing.

11. The suction device for sucking the obstruction in the respiratory tract according to claim 9, wherein an outer side of the housing comprises an air pressure sensor and a display electrically connected to the air pressure sensor.

12. The suction device for sucking the obstruction in the respiratory tract according to claim 9, wherein the connector comprises a base plate; an upper side of the base plate is provided with a hollow upper connecting cylinder, the upper connecting cylinder is inserted in the opening, and an outer side of the upper connecting cylinder is hermetically connected to an inner side of the opening; a lower side of the base plate is provided with a hollow lower connecting cylinder, the first connecting cylinder is inserted in the lower connecting cylinder, and an outer side of the first connecting cylinder is hermetically connected to an inner side of the lower connecting cylinder; and a central axis of the lower connecting cylinder and a central axis of the upper connecting cylinder form a certain included angle.

13. The suction device for sucking the obstruction in the respiratory tract according to claim 9, wherein the connector is further provided with an opening hole, an external check valve is arranged in the opening hole, and the external check valve can allow a gas in a housing of the connector to flow out to an outside.

14. A suction device for sucking an obstruction in a respiratory tract, the suction device comprising:

a negative pressure generator and a mask, wherein the mask is communicated with the negative pressure generator by means of a connector;

the connector comprises a base plate, the base plate is provided with a through air vent;

the negative pressure generator comprises a housing and a piston rod movably inserted in the housing, the housing is internally provided with an axially through cavity, an upper end of the housing is provided with an avoidance hole communicated with the cavity, and a lower end thereof is provided with an opening communicated with the cavity;

the piston rod comprises a push-pull rod and a piston sleeved on the push-pull rod, an upper end of the push-pull rod runs through the avoidance hole, and an outer side wall of the piston is movably and hermetically connected to an inner side wall of the housing by means of a sealing ring;

wherein a diameter of the push-pull rod is smaller than a diameter of the housing; and a mask body includes an internal space that is connected to a lower end of a through first connecting cylinder, and a flexible annular pad is arranged on a lower edge of the mask body, wherein the mask omits an elastic throat tube such that the elastic throat tube cannot enter a mouth of a patient, and wherein the connector is further provided with an opening hole, the opening hole runs through the base plate of the connector, a lower end of the opening hole is communicated with an outside.

15. The suction device for sucking the obstruction in the respiratory tract according to claim 14, wherein the connector comprises an upper side of the base plate is provided with a hollow upper connecting cylinder, the upper connecting cylinder is inserted in the opening, and an outer side of the upper connecting cylinder is hermetically connected to an inner side of the opening.

16. The suction device for sucking the obstruction in the respiratory tract according to claim 14, wherein the connector comprises a lower side of the base plate is provided with a hollow lower connecting cylinder, the first connecting cylinder is inserted in the lower connecting cylinder, and an outer side of the first connecting cylinder is hermetically connected to an inner side of the lower connecting cylinder.

17. The suction device for sucking the obstruction in the respiratory tract according to claim 14, wherein the mask is detachably connected to the connector, so that the mask can be replaced with a mask with a different shape and size based on a rescued patient.

18. A suction device for sucking an obstruction in a respiratory tract, the suction device comprising:

a negative pressure generator and a mask, wherein the mask is communicated with the negative pressure generator by means of a connector;

the negative pressure generator comprises a housing and a piston rod movably inserted in the housing, the housing is internally provided with an axially through cavity, an upper end of the housing is provided with an avoidance hole communicated with the cavity, and a lower end thereof is provided with an opening communicated with the cavity;

the piston rod comprises a push-pull rod and a piston sleeved on the push-pull rod, an upper end of the push-pull rod runs through the avoidance hole, and an outer side wall of the piston is movably and hermetically connected to an inner side wall of the housing by means of a sealing ring such that when the piston rod moves towards the lower end of the housing, a check valve in an air vent prevents gas from flowing into an interior of the mask; when the piston moves towards the upper end of the housing, the check valve in the air vent allows the gas inside the mask to flow into the housing;

wherein a diameter of the push-pull rod is smaller than a diameter of the housing; wherein the mask consists only of a mask body, a through first connecting cylinder, and a flexible annular pad; and the mask body includes an internal space that is connected to a lower end of the through first connecting cylinder, and the flexible annular pad is arranged on a lower edge of the mask body, and wherein the mask omits an elastic throat tube such that the elastic throat tube cannot enter a mouth of a patient.

19. The suction device for sucking the obstruction in the respiratory tract according to claim 18, wherein the suction device is configured such that after the flexible annular pad of the mask surrounds a mouth of a patient, the mask is able to be held to keep a seal between the mask and a face of the patient, and when the piston rod is pulled upward, a vacuum suction is formed in the cavity of the housing and in the internal space of the mask body through the through first connecting cylinder such that when the mask is lifted to release a negative pressure created by the vacuum suction, a strong suction force in the respiratory tract is formed.

20. The suction device for sucking the obstruction in the respiratory tract according to claim 18, wherein when the piston rod is pushed to a bottommost end, the piston abuts against the connector; and when the piston rod is pushed to the bottommost end, any foreign bodies are discharged while internal air in the housing is discharged.

21. The suction device for sucking the obstruction in the respiratory tract according to claim 18, wherein the mask body is hemispherical, a lower edge of the mask body is circular, and the flexible annular pad is circular.

\*    \*    \*    \*    \*